United States Patent [19]

Davis, Jr. et al.

[11] Patent Number: 5,113,420

[45] Date of Patent: May 12, 1992

[54] METHOD AND APPARATUS FOR POSITIONING A SAMPLE WITH REPEATABLE ACCURACY

[75] Inventors: Lorne A. Davis, Jr., Houston; Gregory P. Pepin, Sugar Land; David L. Gebert, Houston, all of Tex.

[73] Assignee: Texaco Inc., White Plains, N.Y.

[21] Appl. No.: 632,561

[22] Filed: Dec. 24, 1990

[51] Int. Cl.⁵ ............................ H05G 1/60; A61B 6/04
[52] U.S. Cl. ...................................... 378/20; 378/177; 378/209; 378/195
[58] Field of Search ................ 378/20, 208, 209, 177, 378/195

[56] References Cited

U.S. PATENT DOCUMENTS

| | | | |
|---|---|---|---|
| 4,034,224 | 7/1977 | Heavens et al. | 378/20 |
| 4,131,802 | 12/1978 | Braden et al. | 378/20 |
| 4,583,242 | 4/1986 | Vinegar et al. | 378/20 |
| 4,688,278 | 8/1987 | Van Aspert | 378/209 |
| 4,827,761 | 5/1989 | Vinegar et al. | 378/208 |
| 4,914,682 | 4/1990 | Blumenthal | 378/20 |

Primary Examiner—Janice A. Howell
Assistant Examiner—Kim-Kwok Chu
Attorney, Agent, or Firm—Jack H. Park; Kenneth R. Priem; Russell J. Egan

[57] ABSTRACT

An apparatus for moving samples through a CAT scanner is comprised of a driver table assembly and a follower table assembly. The assemblies are fixedly positioned in aligned spaced condition on opposite sides of a CAT scanner and are adapted to move a sample therethrough with great linear accuracy. The driver table assembly is the active member in moving the sample while the follower table assembly is passive in responding to movement of the driver table assembly. Both table assemblies have lathe heads mounted thereon for securing the sample therebetween in a self-centering manner.

8 Claims, 5 Drawing Sheets

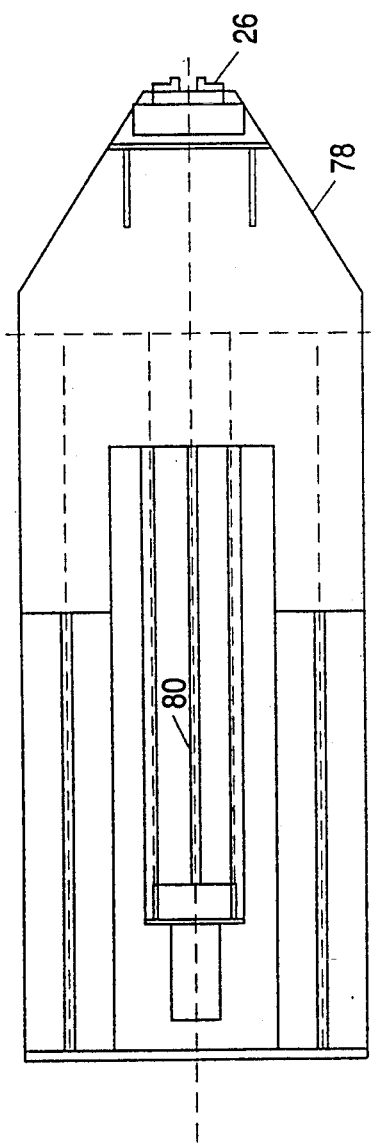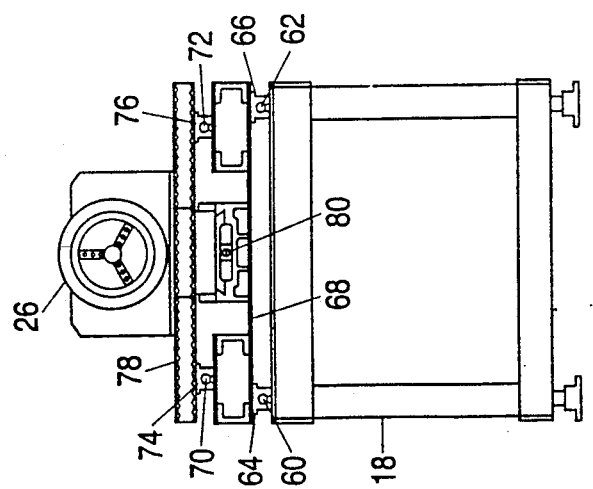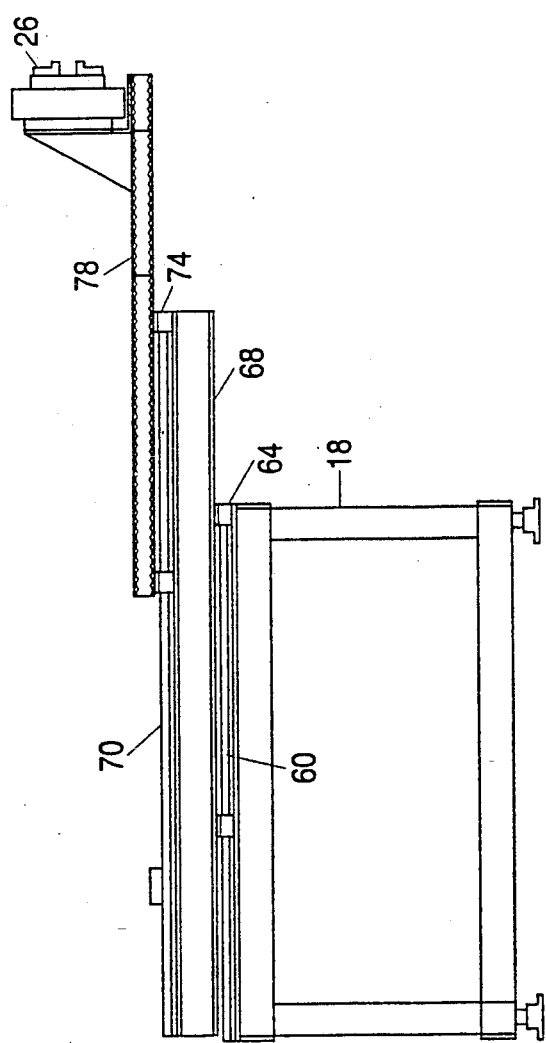
FIG. 5
FIG. 6
FIG. 4

METHOD AND APPARATUS FOR POSITIONING A SAMPLE WITH REPEATABLE ACCURACY

BACKGROUND OF THE INVENTION

1. The Field of the Invention

The present invention relates to a method and apparatus for positioning core samples for x-ray computed tomography measurements and in particular to a method and apparatus which will repeatedly accurately position such core samples.

2. The Prior Art

Computerized axial tomographic scanners (hereinafter referred to as "CAT" scanners) are well-known devices for providing an image of a sample that has spatial resolution in the axial direction that is smaller than the width of the x-ray beam. CAT scanners are widely used, for example, in the medical industry to scan a patient in an attempt to diagnose various medical problems. The patient is supported on a table that moves the patient through the scanning device at a controlled rate.

Accurate and repeatable positioning of core samples during x-ray computed tomography measurements is critical for performing many petrophysical measurements such as porosity distributions and fracture direction, size, and porosity. The sample positioning system that is provided with the standard CAT scanner, namely a patient table, is designed for use in positioning people who are relatively much less heterogeneous than rocks. Major requirements for patient tables are the patient comfort and the ability to support patients of varying sizes and weights while repeatability of the positioning for any one patient is much less critical.

The present invention replaces the known patient table with an improved table assembly which mimics all capabilities of the patient table. In addition, it positions a sample for scanning with accuracy and repeatability not theretofore possible. The improvement in accuracy of positioning is by a factor of from one millimeter, in the prior art tables, to 0.02 millimeters for the subject table assembly. The present invention automatically centers the sample to be scanned within a scanning circle thereby alleviating the need to perform numerous test scans heretofore required to verify sample centering. It also eliminates the need for shims or like means to reposition or adjust the position of the sample in order to achieve the desired position. The control means of the present invention is compatible with that of standard CAT scanner hardware and software. This enables the present invention to be readily exchanged for the patient table assembly means commonly provided with a CAT scanner thereby obviating the requirement for even minor modifications in order for the present invention to be used.

The present invention comprises a specialized table assembly which serves as a replacement for the standard patient positioning table of known CAT scanners. Such a patient table is inadequate for supporting and moving geological cores and other non-biological samples, during the actual scanning process.

The subject table is particularly suitable for use with Technicare model 2020HR and 2060 CAT scanners.

SUMMARY OF THE INVENTION

The present invention consists of a pair of cooperating table assemblies, namely a drive table assembly and a follower table assembly. The drive table assembly is placed on one side of the CAT scanner gantry and the follower table assembly is placed in a spaced and aligned relationship on the opposite side to the gantry. Machine tool quality lathe heads are mounted on each table assembly and are adapted to grip the opposite ends of the sample to be scanned. Because the lathe heads are self-centering devices, samples of any size will be automatically centered with respect to the scan circle of the CAT scanner. The two-table design obviates one problem which would be encountered with a standard patient table, namely sagging caused by the normally long and heavy petrophysical samples. The present invention positively grips the core samples by their ends rather than having the core centrally supported with the ends extending off the ends of the patient table. A computer controlled high resolution screw drive means in the drive table assembly replaces the bicycle chain drive means of a patient table. A feedback loop, via a linear position encoder, is used to position the sample with an accuracy of 0.02 millimeters, rather than the accuracy of one millimeter used on a standard medical table. Both the subject drive table assembly and the follower table assembly can be removed from their positions relative to the gantry to allow normal maintenance of the system.

The control electronics of the drive table assembly are designed to enable the table to perform all types of motion performed by the patient table, namely manual positioning through pushbuttons on the gantry, automatic positioning controlled by the CAT scanner software, and "Radiographic scanning," called Deltaview ® by Technicare Corporation of Cleveland, Ohio.

BRIEF DESCRIPTIONS OF THE DRAWINGS

The present invention will now be described by way of example with reference to the accompanying drawings in which:

FIGS. 4 to 6 are a side elevation, top plan, and end view, respectively, of the drive table assembly of the present invention in an extended position.

DETAILED DESCRIPTION OF THE PREFERRED EMBODIMENT

Figure 1:
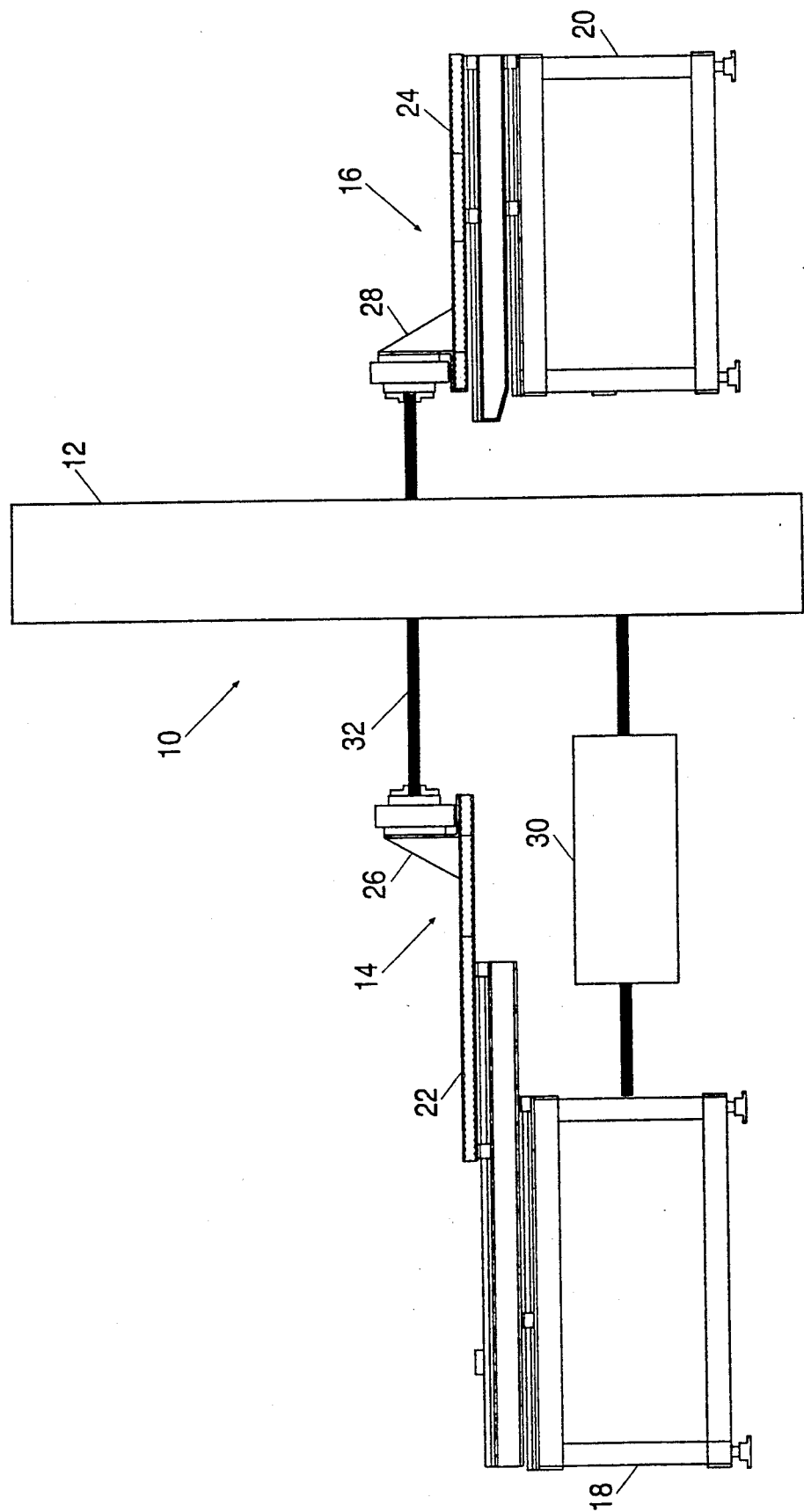
FIG. 1 is a schematic side elevation showing positioning of a sample relative to a CAT scanner gantry by the positioning device of the present invention.

The components of the present invention are schematically shown in FIG. 1 in association with a conventional CAT scanner 10. The scanner is of a well known type and only the gantry portion 12 through which the sample to be scanned is passed has been shown for simplicity of the drawings. A typical CAT suitable for use with the present invention is the Model 2060 or 2020HR manufactured by Technicare Corporation of Cleveland, Ohio. This typically contains an X-ray source, collimator means, filters and detectors, none of which have been shown as they and their function are well known and are not essential for an understanding of the present invention.

The present invention has a drive table assembly 14 located on a first side of the gantry and a follower table assembly 16 on the opposite side of the gantry in aligned and spaced position with respect to the drive table assembly. The table assemblies are substantially identical with the exception being that the drive table assembly 14 includes drive train means to be discussed later. Each table assembly 14,16 has a base portion 18,20, an extendable table portion 22,24, and a mounting portion 26,28 supported on the free end of the table portion. Each base portion can be provided with known retractable wheel means (not shown) to facilitate positioning of the assembly and stabilization means (also not shown) to assure there will be substantially no movement when in use. Each mounting portion 26,28 comprises a turret lathe head of known configuration. The base portions are set so that the respective lathe heads are in opposing, spaced, axially aligned relationship. Control means 30 electrically connect the drive means (not shown) of the drive table to the control section of the gantry (also not shown) to provide a controlled relative movement of the core sample 32 through the gantry. The follower table assembly 20 is a passive device and reacts to the movement of the sample supported between the lathe heads 26,28. As the drive table 14 moves from a retracted condition to an extended condition (see FIG. 3), the follower table assembly does the reverse movement by going from an extended to a retracted condition (see FIG. 6).

Figure 2:
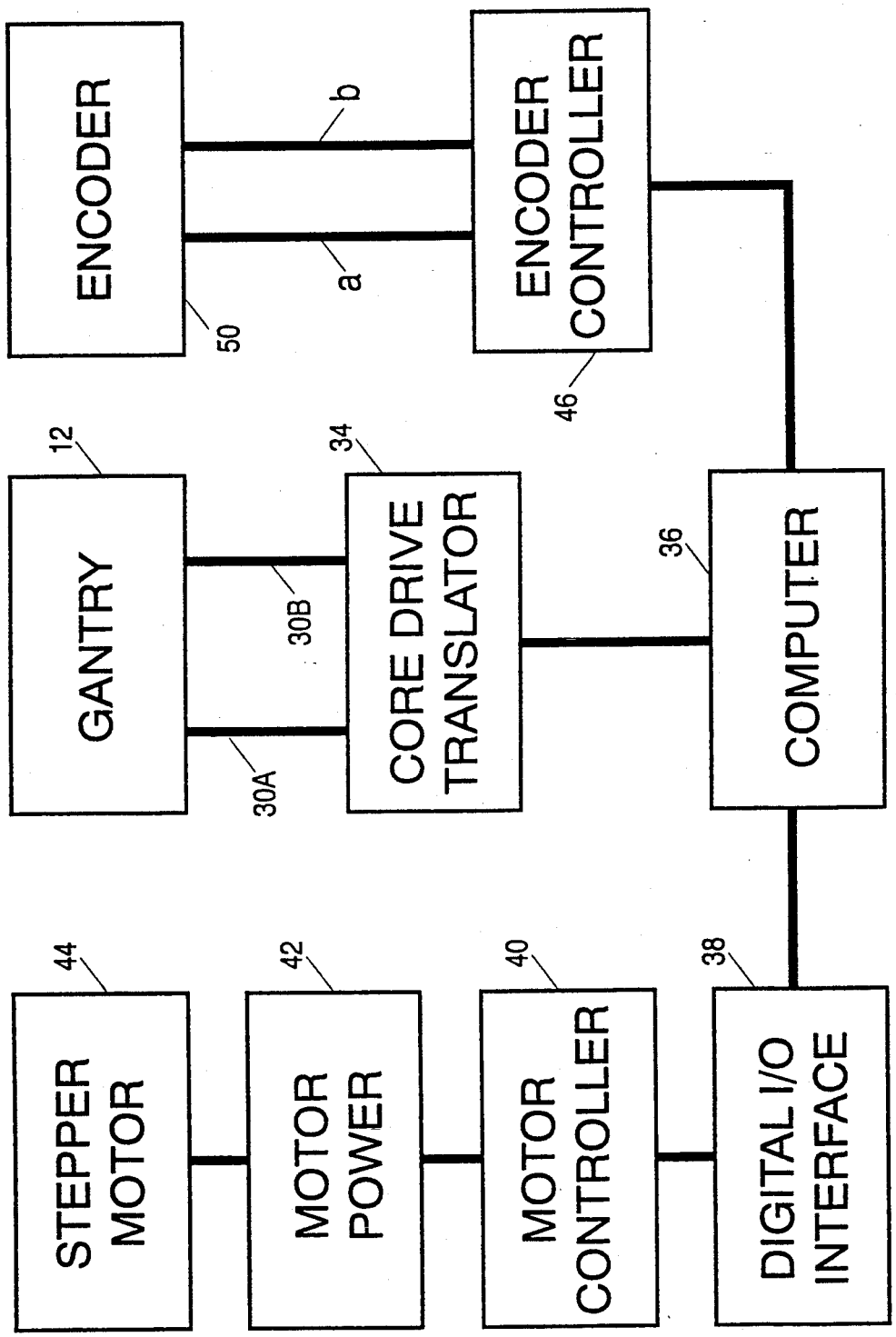
FIG. 2 is a block level schematic of the components of the subject system.

A block level diagram of the connection of the drive means of the drive table and the gantry is shown in FIG. 2. The gantry 12 is connected to the drive table assembly 14 by control means 30 which includes both control lines 30A and feedback lines 30B. This is received in a gantry controller 34 in the drive table with the controller being connected to a computer 36. A first output of the computer 36 goes through a digital interface 38 to the motor controller 40 and to power supply 42 to cause a stepper motor 44 to drive the extendable table portion 22 of drive table assembly 14. An output of the gantry encoder controller 46 goes to the computer 36 to provide table position feedback.

The components shown in this figure, with the exception of the gantry, are part of the present invention. The control lines 30A and 30B from the gantry 12 feed information to the drive table assembly 14 as to the desired direction and speed of motion. These are used by the computer 36 for controlling the stepper motor 44 that drives the extendable table portion 22. The feedback lines to the gantry are the position information provided by the linear position encoder 50. The encoder 50 provides two sets of TTL level signals "a" and "b" which are 90 degrees out of phase. The encoder produces 25 pulses per millimeter of motion for each channel. One of these is reduced to 1 pulse per millimeter by the gantry controller 34 for use by the gantry 12. Both signals are sent to the encoder controller 46 for use by the computer 36 to internally verify proper table movement.

Figure 3:
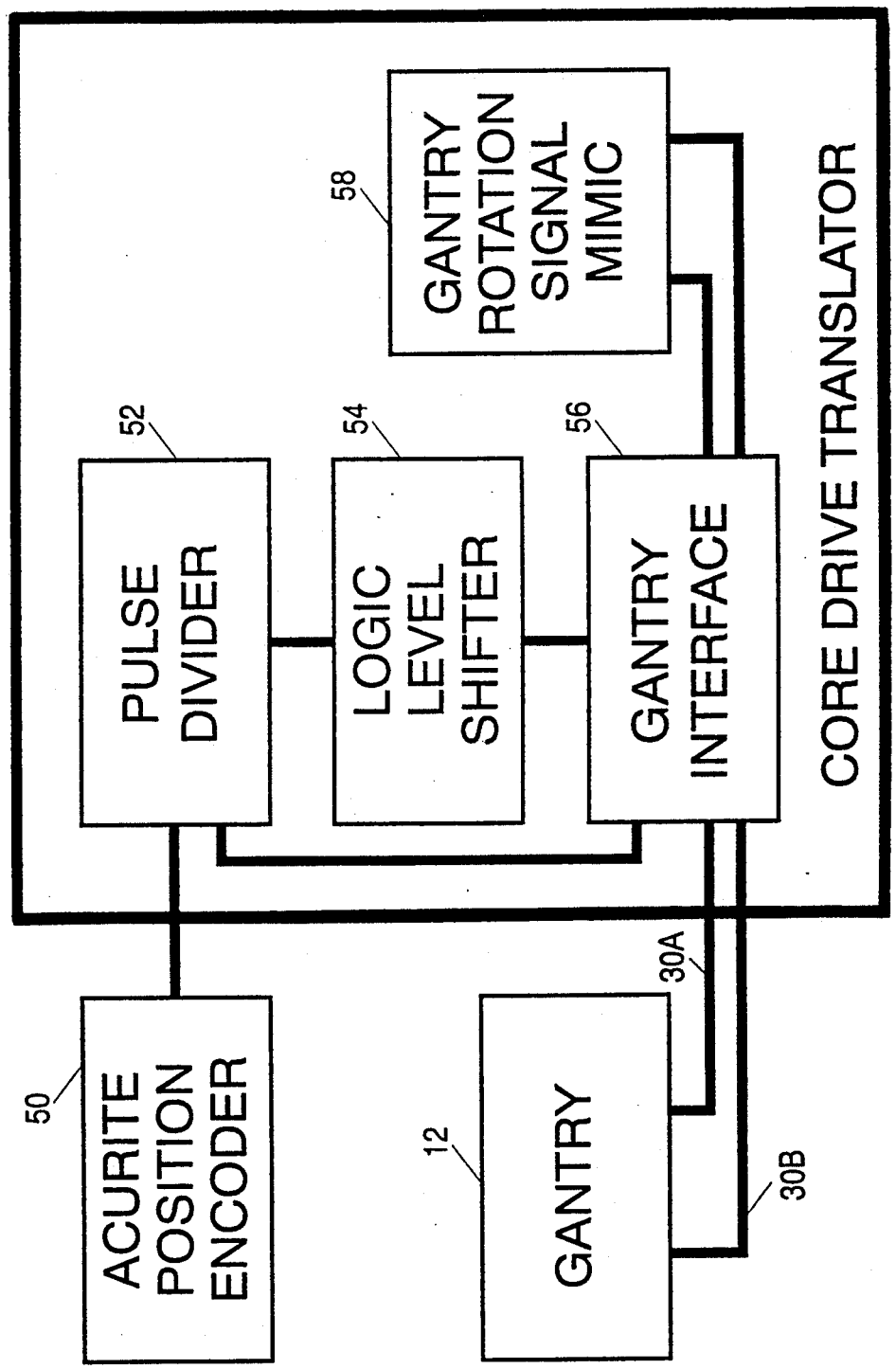
FIG. 3 is a block level schematic of the control apparatus of the present invention.

FIG. 3 is a more detailed block diagram of the gantry controller 34 noted in FIG. 2. The TTL level signal (25 pulses per millimeter) from the Accurite position encoder 50 is fed into a pulse divider 52 that produces one TTL level signal output for each 25 signals received. This signal is fed into a logic level shifter 54 that modifies the signal from TTL level to HCMOS level and inverts it to provide the signal levels desired by the gantry. This signal is fed into the gantry interface 56 which transmits the signal to the gantry 12 over the lines 30B. One of the control lines 30A is connected to the gantry interface 56 and is used t enable the pulse divider circuit 52 and a gantry rotation mimic circuit 58. The gantry rotation mimic circuit 58 is needed to allow the radiograph scanning (Deltamines) mentioned earlier. It provides two sets of TTL level signals that are produced at a rate of 8 pulses per millimeter of table motion. These are sent to the gantry 12 through the gantry interface 56.

Details of the drive table assembly 14 are shown in FIGS. 4, 5 and 6. The drive table assembly 14 shown in FIGS. 4, 5 and 6 has a fixed base 18 fixedly supporting a first pair of optically straight shafts 60,62 on an upper surface thereof. Pillow block assemblies 64,66, each assembly having at least four pillow blocks, support a lower positioning table portion 68 of the table assembly on the shafts 60,62. A second pair of optically straight shafts 70,72 are mounted on the top of lower positioning table portion 68 and a similar pair of pillow block assemblies 74,76 support a traveling table 78 thereon. The lathe head 26 is fixedly mounted on the free end of travelling table 78. Screw drive means 80 are connected to move the travelling table portion 78 relative to the lower positioning table 68, the latter being used to initially position the core sample 32 with respect to the gantry 12. The upper travelling table 78 is used in cooperation with the like travelling table of the follower table assembly to move the sample through the CAT scanner at a controlled rate.

Figure 9:
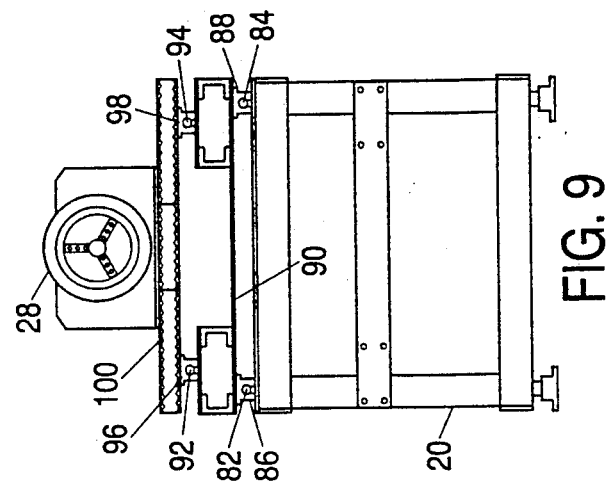
FIGS. 7 to 9 are a side elevation, top plan, and end view, respectively, of the follower table assembly of the present invention in a retracted position.
Figure 8:
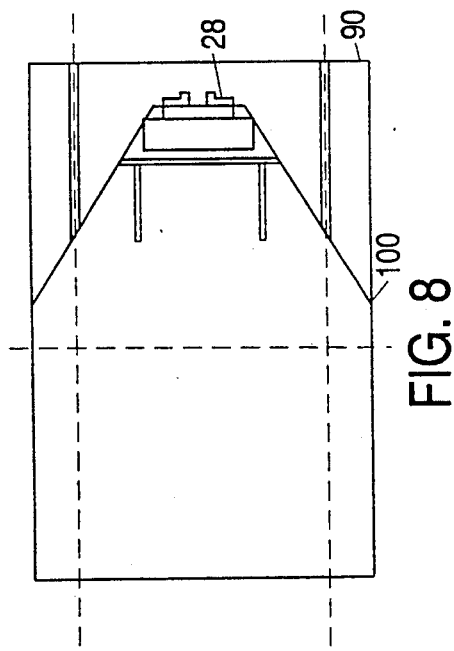
Figure 7:
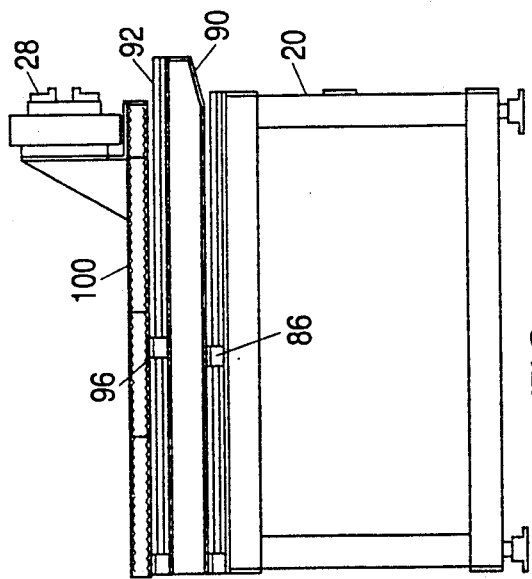

The follower table assembly 16 is shown in FIGS. 7, 8 and 9 and is essentially the same as the above described drive table assembly 14, lacking only the drive means 80. A first pair of optically straight shafts 82,84 are fixedly mounted on the base 20 in parallel spaced fashion. Pillow block assemblies 86,88 support a lower positioning table 90 thereon. A second pair of optically straight shafts 92,94 are mounted on the upper surface of the positioning table 90. Pillow block assemblies 96,98 support the traveling table 100 thereon. The lathe head 28 is fixedly mounted on the free end of the travelling table 100. The follower table assembly 16 is shown in FIGS. 7, 8 and 9 in a retracted position, which is the position the table assembly would be in at the end of a scanning run or during scanner maintenance. The follower table assembly 16 would be initially set in the proper position to grip one end of the core sample 32. This position is determined by both position of the drive table assembly 14 and the sample size. The follower table assembly would be driven to the position shown in FIGS. 7, 8 and 9 as the sample 32 is moved through the CAT scanner.

The method for utilizing the present invention to perform a CAT scan on a petrophysical sample are known. A suitable method is described in U.S. Pat. No. 4,635,197, the disclosure of which is incorporated herein by reference.

The present invention may be subject to many modifications and changes without departing from the spirit or essential characteristics thereof. The present embodiment should be therefore be considered in all respects as illustrative and not restrictive of the scope of the invention.

I claim:

1. An apparatus for repeatedly positioning a sample accurately and for moving said sample relative to an associated device, said apparatus comprising:

a driver table assembly and a follower table assembly in spaced and aligned condition relative to said associated device to move a sample axially relative to said device;

each said table assembly having a base portion with means to fixedly position it relative to said device, movable sample positioning means supported by said base and having a positioning table moveably mounted on said base with means on said positioning table to fix it relative to said base for initially positioning said sample relative to said device, means on said sample positioning table to engage one end of said sample;

said drive table assembly further comprising drive means to drive said sample positioning means of said drive table assembly relative to said drive table assembly whereby said sample is moved relative to said device.

2. An apparatus according to claim 1 wherein said positioning means further comprises a sample transporting table movable with respect to said positioning table, said transporting table of said drive table assembly being operatively connected to said drive means whereby a sample supported thereby is moved relative to said device.

3. An apparatus according to claim 2 wherein said sample positioning means comprises a turret lathe head fixedly mounted on a free end of said transporting table.

4. An apparatus according to claim 1 wherein said drive means is responsive to commands from said associated device for moving said sample relative thereto.

5. An apparatus according to claim 1 wherein said associated device is a CAT scanner preforming tomographic scanning of the sample.

6. An apparatus according to claim 1 wherein said sample is a petrophysical sample.

7. An apparatus according to claim 1 wherein said drive means comprises:

control means in said device having both control and feedback connections to the drive means of said drive table assembly;

computer means in said drive means connected to receive an output from said control means;

digital I/O interface means responsive to said computer means;

motor controller means responsive to said digital I/O interface output;

motor power means responsive to said motor controller means; and stepper motor means responsive to motor power means and connected to drive said positioning table accordingly.

8. An apparatus according to claim 7 wherein said control means comprises: a position encoder;

pulse divider means connected to the output of said position encoder;

logic level means connected to the output of said divider means to provide signals at a useable level; and means responsive to the device for controlling the rate of movement to that necessary to achieve the desired relative movement therebetween.

* * * * *